US012257939B2

(12) United States Patent
Space et al.

(10) Patent No.: US 12,257,939 B2
(45) Date of Patent: Mar. 25, 2025

(54) HEADREST VENTILATION SYSTEMS AND METHODS FOR SEATING ASSEMBLIES

(71) Applicant: THE BOEING COMPANY, Chicago, IL (US)

(72) Inventors: David R. Space, Everett, WA (US);
James A. Fullerton, Bothell, WA (US);
Timothy J. Arnaud, Everett, WA (US);
Jon Burton Shaw, Everett, WA (US);
Stephen M. Trent, Everett, WA (US);
Ty A. Larsen, Everett, WA (US);
Myriam Khalil, Chicago, IL (US)

(73) Assignee: The Boeing Company, Chicago, IL (US)

( * ) Notice: Subject to any disclaimer, the term of this patent is extended or adjusted under 35 U.S.C. 154(b) by 448 days.

(21) Appl. No.: 17/405,359

(22) Filed: Aug. 18, 2021

(65) Prior Publication Data

US 2022/0118899 A1    Apr. 21, 2022

Related U.S. Application Data

(60) Provisional application No. 63/094,370, filed on Oct. 21, 2020.

(51) Int. Cl.
*B60N 2/879* (2018.01)
*A61L 9/20* (2006.01)
*B60N 2/56* (2006.01)

(52) U.S. Cl.
CPC ............... *B60N 2/879* (2018.02); *A61L 9/20* (2013.01); *B60N 2/5635* (2013.01); *B60N 2/565* (2013.01)

(58) Field of Classification Search
CPC ............... B60N 2/879; B64D 11/0646; B64D 11/0626; B64D 2013/0651; A61L 9/20
(Continued)

(56) References Cited

U.S. PATENT DOCUMENTS 9,845,034 B1 * 12/2017 Lew ....................... B60N 2/242
10,029,797 B2 * 7/2018 Space .................... B64D 11/06
(Continued)

FOREIGN PATENT DOCUMENTS

FR         3028453       5/2016
WO    WO 96/09205       3/1996

OTHER PUBLICATIONS

Extended European Search Report for EP 21193015.1-1010, dated Feb. 4, 2022.

*Primary Examiner* — Allen R. B. Schult
(74) *Attorney, Agent, or Firm* — Joseph M. Butscher; The Small Patent Law Group LLC

(57) ABSTRACT

A headrest ventilation assembly is configured to secure to a headrest of a seat assembly, and includes an air conduit including one or more air inlets and one or more air outlets, and an air filter disposed within the air conduit between the one or more air inlets and the one or more air outlets. The air filter is configured to remove contaminants from the air that is drawn into the air conduit before being delivered out of the one or more air outlets. The assembly can also include a fan disposed on or within the air conduit. The fan is configured to draw the air into the one or more air inlets and provide airflow to deliver the air out of the one or more air outlets. The assembly can also include one or more ultraviolet (UV) light emitters disposed on or within the air conduit. The UV light emitter(s) are configured to emit UV light into the air to sanitize the air before the air is delivered out of the one or more air outlets.

20 Claims, 7 Drawing Sheets

(58) Field of Classification Search
USPC .......................................................... 454/69
See application file for complete search history.

(56) References Cited

U.S. PATENT DOCUMENTS

| | | | |
|---|---|---|---|
| 2002/0098127 A1* | 7/2002 | Bollini | A61L 9/20 |
| | | | 250/436 |
| 2008/0175426 A1* | 7/2008 | Jacobs | B60R 11/0217 |
| | | | 381/376 |
| 2014/0179212 A1 | 6/2014 | Space | |
| 2018/0079368 A1* | 3/2018 | Pirri | B60N 2/879 |
| 2022/0054699 A1* | 2/2022 | Nakama | F24F 7/003 |

* cited by examiner

HEADREST VENTILATION SYSTEMS AND METHODS FOR SEATING ASSEMBLIES

CROSS-REFERENCE TO RELATED APPLICATIONS

This application relates to and claims priority benefits from U.S. Provisional Application No. 63/094,370, entitled "Headrest Ventilation Systems and Methods for Seating Assemblies," filed Oct. 21, 2020, which is hereby incorporated by reference in its entirety.

FIELD OF THE DISCLOSURE

Examples of the subject disclosure generally relate to headrest ventilation systems and methods for seating assemblies, such as within internal cabins of vehicle.

BACKGROUND OF THE DISCLOSURE

Vehicles such as commercial aircraft are used to transport passengers between various locations. Many commercial vehicles such as aircraft have High Efficiency Particulate Air (HEPA) filters in air conditioning systems that are able to entrap microbes and pathogens. The HEPA filters receive and clean air exiting the cabin or about to enter the cabin. HEPA filters and frequent cleaning of the cabin between flights are some methods to ensure the health of the passengers and crew onboard the aircraft.

Further, certain passengers may prefer to wear masks within an internal cabin of a vehicle in order to reduce the risk of spreading pathogens. However, wearing masks during long flights, for example, may be uncomfortable for certain passengers.

SUMMARY OF THE DISCLOSURE

A need exists for a system and a method for preventing, minimizing, or otherwise reducing the spread of pathogens between passengers onboard a vehicle during a trip, such as between passengers in an internal cabin of an aircraft during a flight, without risking harm to the passengers.

With that need in mind, certain examples of the subject disclosure provide a headrest ventilation assembly configured to secure to a headrest of a seat assembly. The headrest ventilation assembly includes an air conduit including one or more air inlets and one or more air outlets, and an air filter disposed within the air conduit between the one or more air inlets and the one or more air outlets. The air filter is configured to remove contaminants from the air that is drawn into the air conduit before being delivered out of the one or more air outlets.

In at least one example, the headrest ventilation assembly also includes a fan disposed on or within the air conduit. The fan is configured to draw the air into the one or more air inlets and provide airflow to deliver the air out of the one or more air outlets.

In at least one example, the headrest ventilation assembly also includes one or more ultraviolet (UV) light emitters disposed on or within the air conduit. The one or more UV light emitters are configured to emit UV light into the air to sanitize the air before the air is delivered out of the one or more air outlets. As an example, the UV light emitters are configured to emit the UV light at a wavelength within one or both of a far UV spectrum or a UVC spectrum.

In at least one example, the headrest ventilation assembly is separate and distinct from the headrest.

In at least one example, the one or more air inlets are coupled to an air source through a fluid conduit.

In at least one example, the headrest ventilation assembly further includes a housing that contains at least a portion of the air conduit and the air filter.

As an example, the headrest ventilation assembly further includes a covering drape that fits over at least a portion of the headrest. As an example, the air conduit includes one or more both of a plenum or an expandable bellows.

As an example, the headrest ventilation assembly further includes side wings that include the one or more air outlets. The side wings can be moveable between a stowed position and a deployed position.

Certain examples of the present disclosure provide a method for providing a headrest ventilation assembly configured to secure to a headrest of a seat assembly. The method includes providing an air conduit including one or more air inlets and one or more air outlets within the headrest ventilation assembly; disposing an air filter within the air conduit between the one or more air inlets and the one or more air outlets, wherein the air filter is configured to remove contaminants from the air that is drawn into the air conduit before being delivered out of the one or more air outlets; and securing the headrest ventilation assembly to the headrest.

Certain examples of the present disclosure provide a system including a seat assembly including a headrest, and a headrest ventilation assembly secured to the headrest, as described herein.

DETAILED DESCRIPTION OF THE DISCLOSURE

Figure 1:
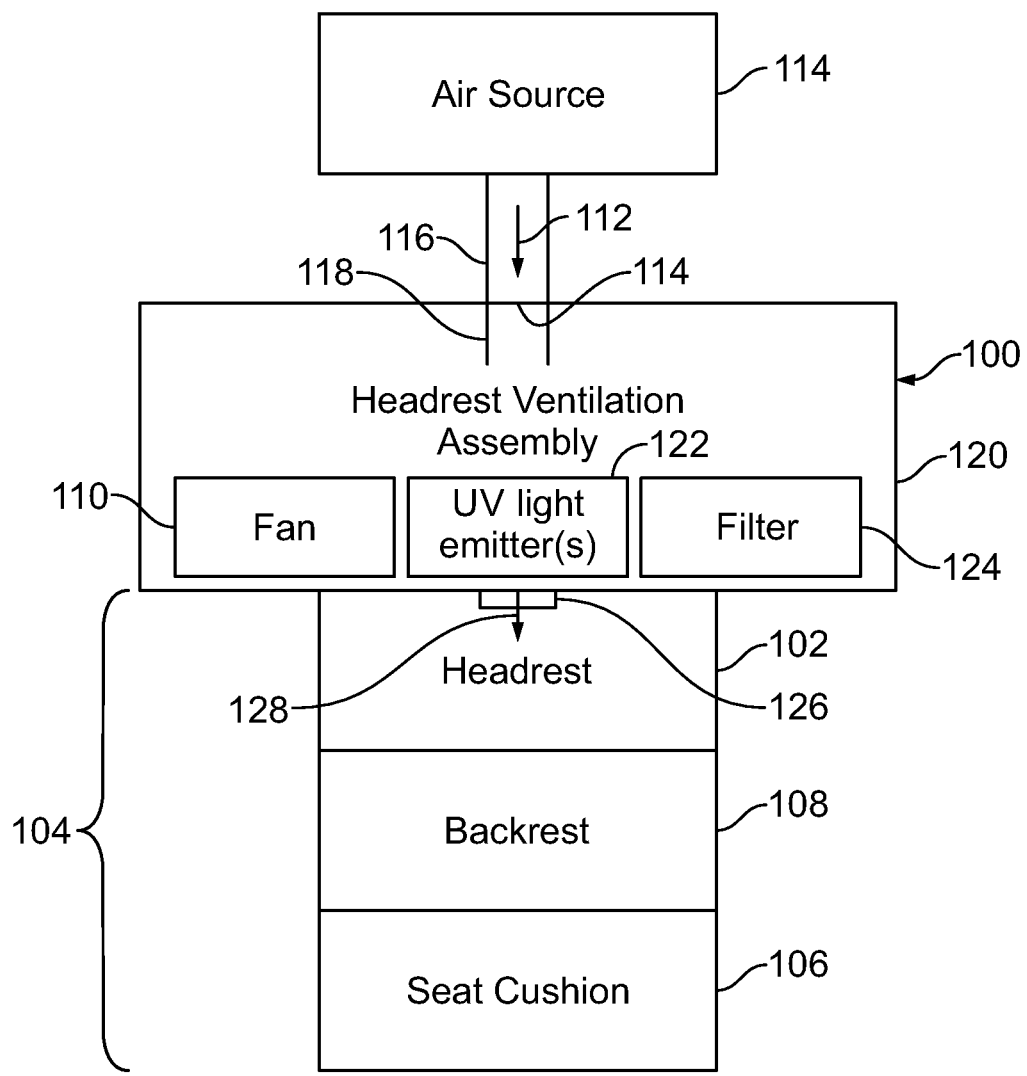
FIG. 1 illustrates a schematic diagram of a headrest ventilation assembly coupled to a headrest of a seat assembly, according to an example of the present disclosure.

The foregoing summary, as well as the following detailed description of certain examples will be better understood when read in conjunction with the appended drawings. As used herein, an element or step recited in the singular and preceded by the word "a" or "an" should be understood as not necessarily excluding the plural of the elements or steps. Further, references to "one example" are not intended to be interpreted as excluding the existence of additional examples that also incorporate the recited features. Moreover, unless explicitly stated to the contrary, examples "comprising" or "having" an element or a plurality of elements having a particular condition can include additional elements not having that condition.

Certain examples of the subject disclosure provide a ventilation system including a seat assembly having a headrest ventilation assembly. The headrest ventilation assembly provides personal ventilation to an individual seated within the seat assembly. In at least one example, the headrest ventilation assembly includes an air filter, such as a HEPA filter, one or more ultraviolet (UV) light emitters configured to emit UV light into an air stream to sanitize the air, and one or more fans. The air filter, UV light emitters and the fan cooperate to provide clean, purified air into a breathing space of an individual seated within the seat assembly. The system and method eliminate, minimize, or otherwise reduce the spread of pathogens, contaminants, and the like in relation to the individual and other individuals seated proximate to the individual, such as within an internal cabin of a vehicle.

The headrest ventilation assembly is configured to draw in air (such as via the fan(s)), sanitize the air (such as via the air filter and/or the UV light emitters), and deliver the sanitized air to a breathing space of the seat assembly. In at least one example, one or more air outlets, such as nozzles, are formed in the headrest ventilation assembly and/or the headrest of the seat assembly. The sanitized air is delivered to the breathing space through the air outlets. As another example, the sanitized air can be delivered to a hood coupled to the headrest ventilation assembly and/or the headrest of the seat assembly. As another example, the sanitized air can be delivered from the headrest ventilation assembly to a face mask configured to be worn by an individual seated within the seat assembly.

In at least one example, an air source is coupled to the headrest ventilation assembly. The air source provides air to the headrest ventilation assembly, which then sanitizes the air before delivering the air to the breathing space of the seat assembly. The air source can be mounted to the headrest ventilation assembly, or connected to the headrest ventilation assembly through a delivery conduit, such as a hose.

In at least one example, the headrest ventilation assembly can be secured to an existing seat assembly. For example, the headrest ventilation assembly is configured to mount onto a headrest of a seat assembly. Optionally, a seat assembly can be integrally formed with the headrest ventilation assembly.

FIG. 1 illustrates a schematic diagram of a headrest ventilation assembly 100 coupled to a headrest 102 of a seat assembly 104, according to an example of the present disclosure. The seat assembly 104 can be within an internal cabin of a vehicle, such as a commercial aircraft. Optionally, the seat assembly 104 can be within a fixed structure, such as within a room of a residential or commercial building.

The seat assembly 104 includes a seat cushion 106 coupled to a backrest 108. The backrest 108 includes or is otherwise coupled to the headrest 102.

In at least one example, the headrest ventilation assembly 100 secures to the headrest 102. In at least one example, the headrest ventilation assembly 100 is not the headrest 102. Instead, the headrest ventilation assembly 100 mounts onto and/or over the headrest 102. For example, the headrest ventilation assembly 100 can mount onto, around, or over at least portions of the headrest 102. The headrest ventilation assembly 100 can be a portable assembly that is selectively mounted to and removed from the headrest 102. Alternatively, the headrest ventilation assembly 100 can be integrally formed with the headrest 102.

The headrest ventilation assembly 100 includes a fan 110, which draws air 112 into the headrest ventilation assembly 100, such as through one or more air inlets 114. The fan 110 can draw air 112 in from an air source 114, which can be coupled to the air inlet 114 through a fluid conduit 116, such as one or more tube(s), pipe(s), hose(s), and/or the like. Optionally, the headrest ventilation assembly 100 is not coupled to a separate air source. Instead, the headrest ventilation assembly 100 draws the air 112 from an ambient environment, such as an internal cabin of a vehicle.

The air inlet(s) 114 leads to an air conduit 118 contained within a housing 120 of the headrest ventilation assembly 100. The housing 120 contains the air conduit 118, the fan 110, one or more ultraviolet (UV) light emitters 122, and an air filter 124. Optionally, at least a portion of the air conduit 118, a portion of the fan 110, a portion of the UV light emitter(s) 122, and a portion of the air filter 124 can be disposed outside of the housing 120.

The fan 110 is disposed on and/or within the air conduit 118. As such, the fan 110 is able to draw the air 112 into the air conduit 118 and provide airflow through and out of the headrest ventilation assembly 100.

The UV light emitters 122 are disposed on and/or within the air conduit 118. The UV light emitters 122 can be lamp(s), bulb(s), light emitting diode(s), and/or the like that are configured to emit UV light into the air 112 as it passes through the air conduit 118. The UV light emitted into the air 112 sanitizes the air 112, such as by eliminating, killing, or otherwise neutralizing pathogens, such as germs, bacteria, viruses, and the like.

The UV light emitters 122 can be fully contained within the headrest ventilation assembly 100. As such, the UV light emitters 122 may not emit the UV light out of the headrest ventilation assembly 100. As such, an individual seated within the seat assembly 104 is not at risk of being exposed to the UV light.

In at least one example, the UV light emitters 122 are configured to emit the UV light within the far UV spectrum, such as between 220-230 nanometers (nm). For example, the UV light emitters 122 can emit UV light at 222 nm. As another example, the UV light emitters 122 are configured to emit the UV light within the UVC spectrum, such as between 230-280 nm. For example, the UV light emitters 122 can emit the UV light at 254 nm. In at least one example, certain ones of the UV light emitters 122 can emit UV light within the far UV spectrum, while other ones of the UV light emitters 122 can emit UV light within the UVC spectrum. Optionally, the UV light emitters can emit UV light at other UV wavelengths.

In at least one example, the UV light emitters 122 are disposed within the air conduit 118 downstream from the fan 110. Optionally, the UV light emitters 122 can be disposed within the air conduit 118 upstream from the fan 110. Alternatively, the headrest ventilation assembly 100 may not include the UV light emitters 122. For example, the headrest ventilation assembly 100 may include the fan 110 and the air filter 124.

The air filter 124 is disposed on and/or within the air conduit 118. The air filter 124 is configured to remove contaminants from the air 112. For example, the air filter 124 can be a HEPA filter. As another example, the air filter 124 can be a sorbent material. As another example, the air filter 124 can be activated charcoal.

In at least one example, the air filter 124 is disposed within the air conduit 118 downstream from one or both of the fan 110 and/or the UV light emitters 122. Optionally, the air filter 124 can be disposed within the air conduit upstream from the fan 110 and/or the UV light emitters 122. Alternatively, the headrest ventilation assembly 100 may not include the air filter 124. For example, the headrest ventilation assembly 100 may include the fan 110 and the UV light emitter(s) 122.

In operation, the fan 110 draws the air 112 into the air conduit 118 via the air inlet 114. The fan 110 operates to provide an airflow direction that moves the air 112 from the air inlet 114 through the air conduit 118 and out of one or more air outlets 126, such as openings, nozzles, or the like. The air conduit 118 extends from the air inlet(s) 114 to the air outlet(s) 126. The fan 110, the UV light emitters 122, and the air filter 124 are disposed within the air conduit 118 between the air inlet(s) 114 and the air outlet(s) 126.

The air 112 passes through the air conduit 118 of the headrest ventilation assembly 100. As the air 112 passes through the air conduit 118, the UV light emitters 122 emit the UV light into the air 112, thereby sanitizing the air. Further, the air filter 124 removes contaminants from the air 112. As such, purified air 128 is delivered out of the air outlets 126 into a breathing space of an individual seated within the seat assembly 104. The air filter 124, the UV light emitters 122, and the fan 110 cooperate to provide the clean, purified air 128 into the breathing space.

In at least one example, the air outlets 126, such as nozzles, are formed in the headrest ventilation assembly 100. Optionally, the air outlets 126 are formed in the headrest 102 of the seat assembly 104. For example, the air outlets 126 can be formed in the headrest 102 and connected to an air outlet of the headrest ventilation assembly 100, such as via an intermediate conduit. As another example, the purified air 128 can be delivered to a hood coupled to the headrest ventilation assembly 100 and/or the headrest 102 of the seat assembly 104. As another example, the purified air 128 can be delivered from the headrest ventilation assembly 100 to a face mask configured to be worn by an individual seated within the seat assembly 104.

In at least one example, the air source 114 is coupled to the headrest ventilation assembly 100, such as via the fluid conduit 116. The air source 114 provides the air 112 to the headrest ventilation assembly 100, which then sanitizes the air 112 before delivering the air 112 to the breathing space of the seat assembly 104. As an example, the air source 114 can be part of an air conditioning system of a vehicle. As another example, the air source 114 is a portable unit that can be mounted to the headrest ventilation assembly 100, or connected to the headrest ventilation assembly 100 through a delivery conduit, such as a hose.

The air source 114 can be a modular component. The air source 114 can be stowed underneath the seat assembly 104. As another example, the air source 114 can be disposed above the seat assembly 104.

In at least one example, the headrest ventilation assembly 100 can be secured to an existing seat assembly 104. For example, the headrest ventilation assembly 100 is configured to mount onto the headrest 102 of the seat assembly 104. Optionally, the seat assembly 104 can be integrally formed with the headrest ventilation assembly 100.

In at least one example, the headrest ventilation assembly 100 can be a disposable unit. For example, the housing 120 can be formed from paper, cardboard, and/or the like. The headrest ventilation assembly 100 can be replaced after use.

The headrest ventilation assembly 100 can provide airflow on either side of a head of an individual seated within the seat assembly 104. The airflow can be directed into the breathing space and/or into an area surrounding the breathing space, such as into an internal cabin of a vehicle. In an example, the purified air 128 can be delivered to a breathing space from one side (such as via a first side wing of the headrest), flow across the breathing space, and then be exhausted into an opposite side (such as into a second side wing of the headrest). As such, the headrest ventilation assembly 100 can deliver the purified air 128 within the breathing space, proximate to a face of an individual, flow across the breathing space, and exhaled air can be exhausted through and out of the headrest ventilation assembly 100. As such, certain examples create a limited control volume, which reduces energy consumption and improves effectiveness.

As described herein, the headrest ventilation assembly 100 is configured to secure to the headrest 102 of the seat assembly 104. The headrest ventilation assembly 100 includes the air conduit 118 including one or more air inlets 114 and one or more air outlets 126. The air filter 124 is disposed within the air conduit 118 between the one or more air inlets 114 and the one or more air outlets 126. The air filter 124 is configured to remove contaminants from the air 112 that is drawn into the air conduit 118 before being delivered out of the one or more air outlets 126.

In at least one example, the headrest ventilation assembly 100 also includes the fan 110 disposed on or within the air conduit 118. The fan 110 is configured to draw the air 112 into the one or more air inlets 114 and provide airflow to deliver the air 128 out of the one or more air outlets 126.

In at least one example, the headrest ventilation assembly 100 also includes one or more UV light emitters 122 disposed on or within the air conduit 118. The one or more UV light emitters 122 are configured to emit UV light into the air 112 to sanitize the air 112 before the air 112 is delivered out of the one or more air outlets 126.

In at least one example, the headrest ventilation assembly 100 is separate and distinct from the headrest 102. For example, the headrest ventilation assembly 100 couples to (for example, mounts on or over at least a portion of) the headrest 102.

Figure 2:
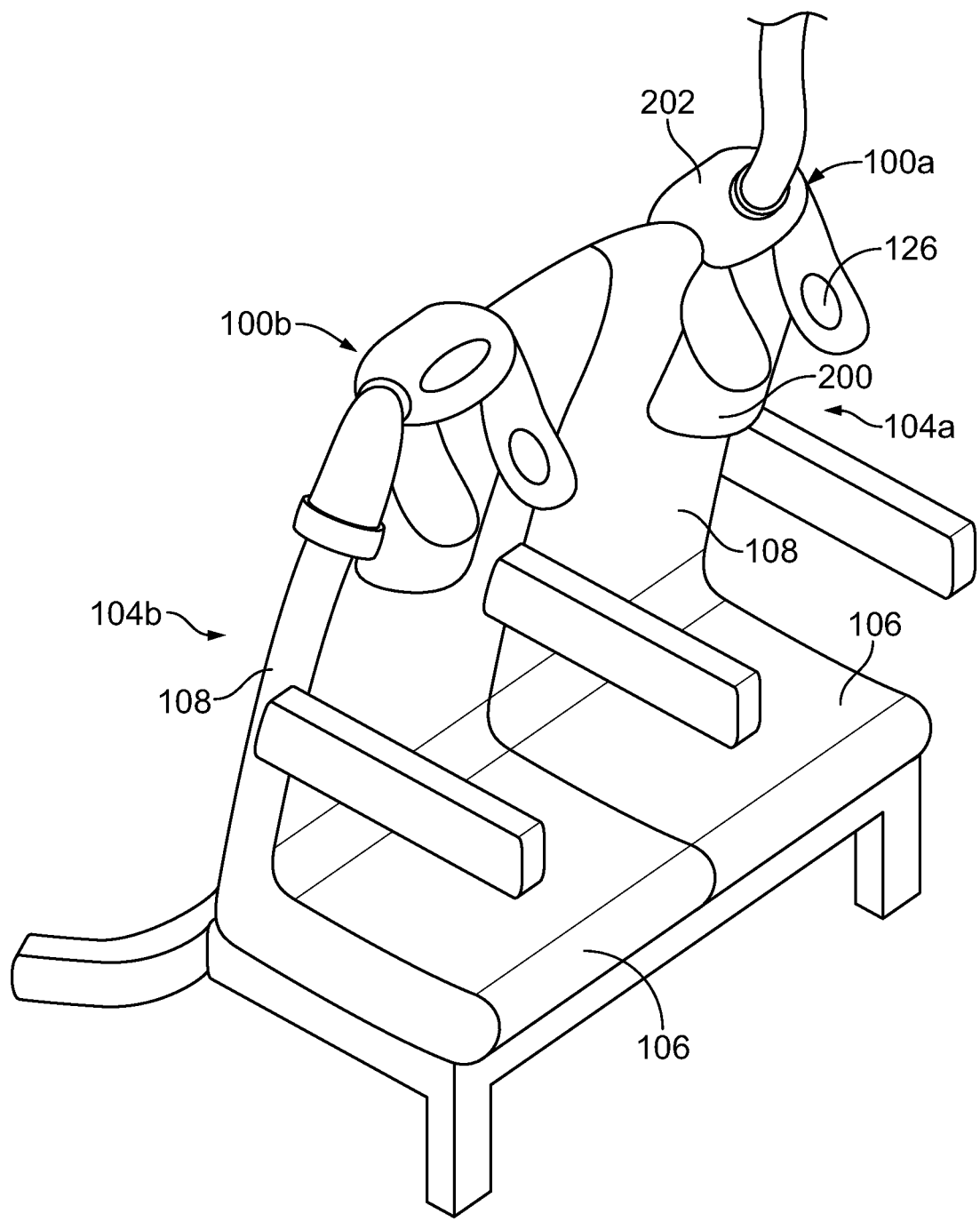
FIG. 2 illustrates a perspective top view of a first seat assembly having a first headrest ventilation assembly, and a second seat assembly having a second headrest ventilation assembly, according to an example of the present disclosure.

FIG. 2 illustrates a perspective top view of a first seat assembly 104a having a first headrest ventilation assembly 100a, and a second seat assembly 104b having a second headrest ventilation assembly 100b, according to an example of the present disclosure. As shown, the first seat assembly 104a and the second seat assembly 104b may be coupled together. Optionally, the first seat assembly 104a and the second seat assembly 104b may not be coupled together. The first headrest ventilation assembly 100a may be of a different type than the second headrest ventilation assembly 100b. Optionally, the same type of headrest ventilation assembly 100 may be coupled to each of the seat assemblies 100a and 100b.

Figure 4:
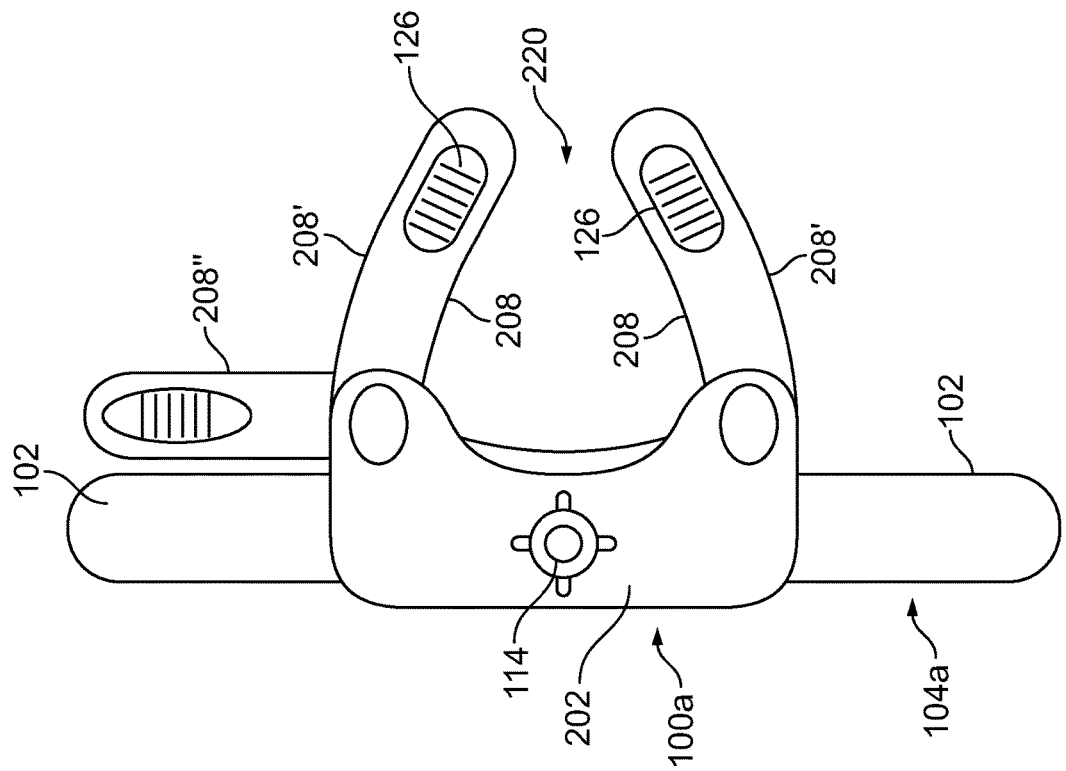
FIG. 4 illustrates a top view of the first headrest ventilation assembly of FIG. 3.
Figure 3:
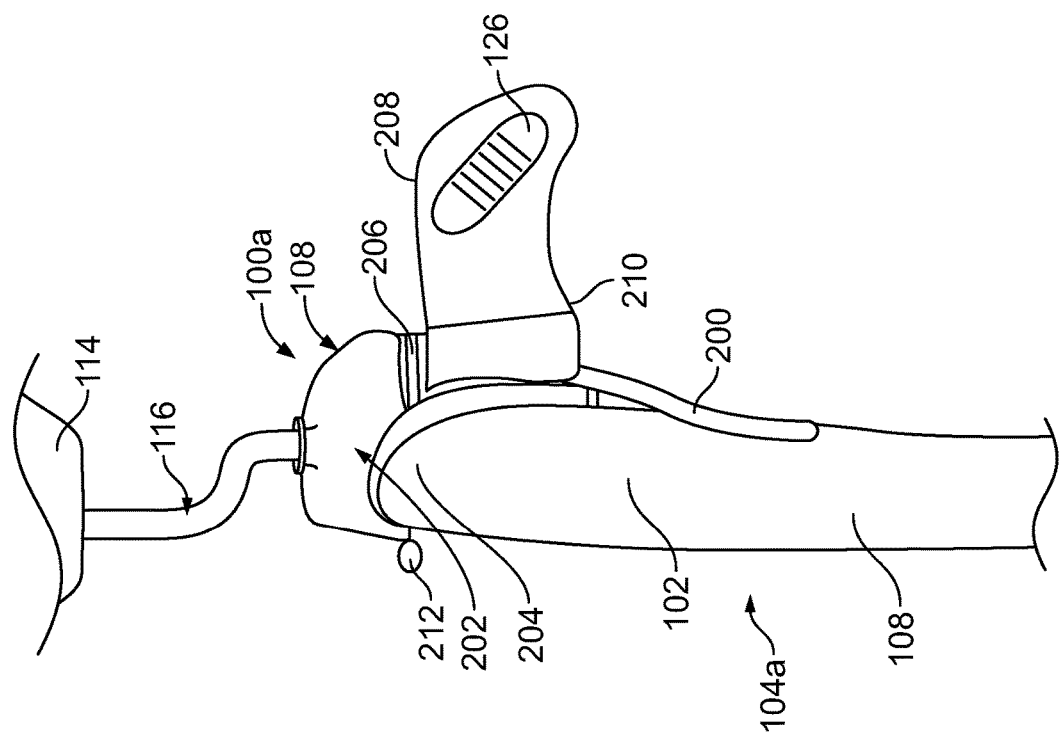
FIG. 3 illustrates a lateral view of the first headrest ventilation assembly mounted over a headrest of the first seat assembly, according to an example of the present disclosure.

FIG. 3 illustrates a lateral view of the first headrest ventilation assembly 100a mounted over the headrest 102 of the first seat assembly 104a. FIG. 4 illustrates a top view of the first headrest ventilation assembly 100a of FIG. 3. Referring to FIGS. 2-4, the headrest ventilation assembly 100a can include a covering drape 200 that fits over the headrest 102. A plenum 202 is coupled to the drape 200 and fits over a top 204 of the headrest 102. As an example, the air conduit 118 shown in FIG. 1 includes the plenum 202.

The plenum 202 is fluidly coupled to an air source 114, such as an air conditioning system of a vehicle or building, through a fluid conduit 116, such as a hose, duct, or the like.

The air conduit 118 can also include an expandable bellows 206 coupled to the plenum 202. The bellows 206 is also mounted on the headrest 102. The bellows 206 can be selectively lengthened or shortened to provide a desired height or otherwise fit for an individual within the seat assembly 104a.

The air conduit 118 fluidly connects to air outlets 126 of side wings 208 of the headrest ventilation assembly 100. The side wings 208 are configured to be disposed on sides of the headrest ventilation assembly 100. Hinges 210 may moveably couple the side wings 208 to the drape 200, for example. The hinges 210 allow the side wings to be selectively moved between stowed and deployed positions. In the deployed positions, the side wings 208 can be spaced from sides of a head of an individual seated within the seat assembly 104a. Optionally, the side wings 208 may not be moveable between stowed and deployed positions.

The headrest ventilation assembly 100a can also include an adjustment member 212 located on a back of the headrest 102. The adjustment member 212 can be a clamp, tie, or the like that allows for the headrest ventilation assembly 100 to be adapted to headrests of varying sizes and shapes.

Referring to FIGS. 1-4, the fan 110, the UV light emitters 122, and the filter 124 can be disposed within the plenum 202, the bellows 206, or the side wings 208. In at least one example, the headrest ventilation assembly 100a may not include the fan 110. Instead, airflow can be provided by one or more fans of the air source 114.

As shown in FIG. 4, the side wings 208 can be in deployed positions 208', such that the side wings 208 are on sides of a breathing space 220. In the deployed positions 208', the air outlets 126 are pivoted away from the headrest 102 of the seat assembly 104a. The side wings 208 can be moved to stowed positions 208". In the stowed positions 208", the side wings 208 can overlay the headrest 102 of the seat assembly 104a.

Figure 6:
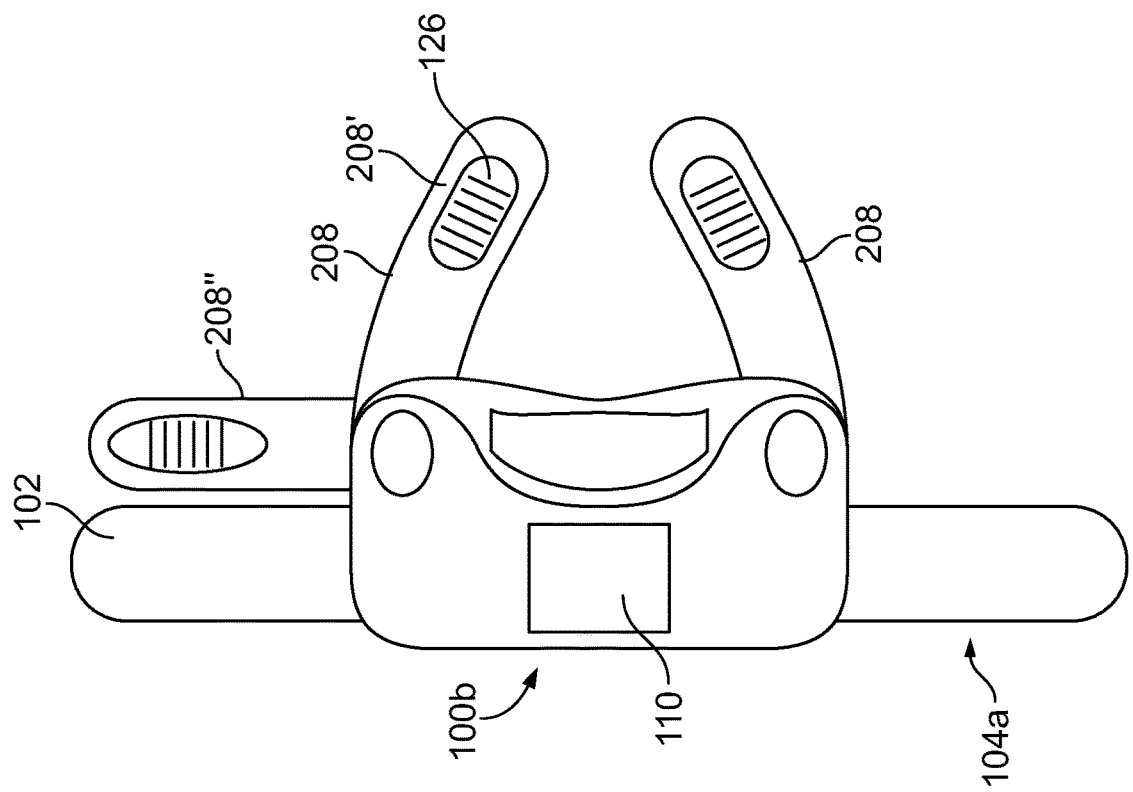
FIG. 6 illustrates a top view of the second headrest ventilation assembly of FIG. 5.
Figure 5:
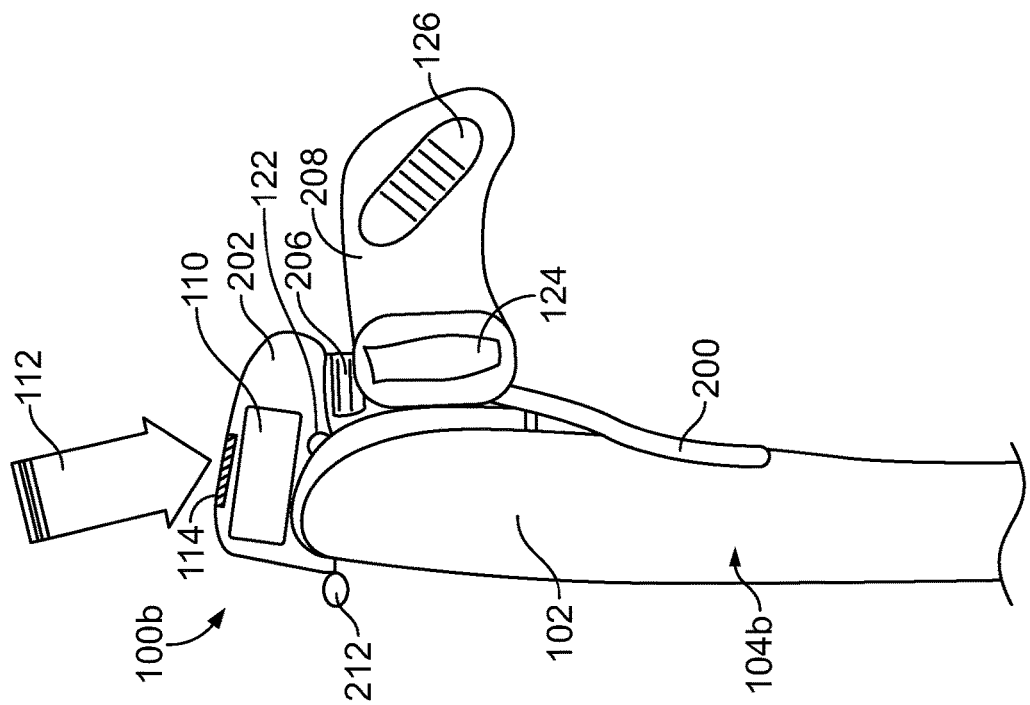
FIG. 5 illustrates a lateral view of the second headrest ventilation assembly mounted over a headrest of the second seat assembly, according to an example of the present disclosure.

FIG. 5 illustrates a lateral view of the second headrest ventilation assembly 100b mounted over a headrest 102 of the second seat assembly 104b, according to an example of the present disclosure. FIG. 6 illustrates a top view of the second headrest ventilation assembly 104b of FIG. 5. Referring to FIGS. 2, 5, and 6, the second headrest ventilation assembly 100b is similar to the first headrest ventilation assembly 100a, except that the second headrest ventilation assembly 100b is not coupled to a separate air source through a conduit. The fan 110 can draw ambient air 112 into the air inlet 114.

The fan 110, the UV light emitter(s) 122, and the air filter 124 can be disposed within various portions of the headrest ventilation assembly 100b. For example, the fan 110, the UV light emitters 122, and/or the air filter 124 can be disposed within the plenum 202, the bellows 206, and/or the side wings 208.

Figure 7:
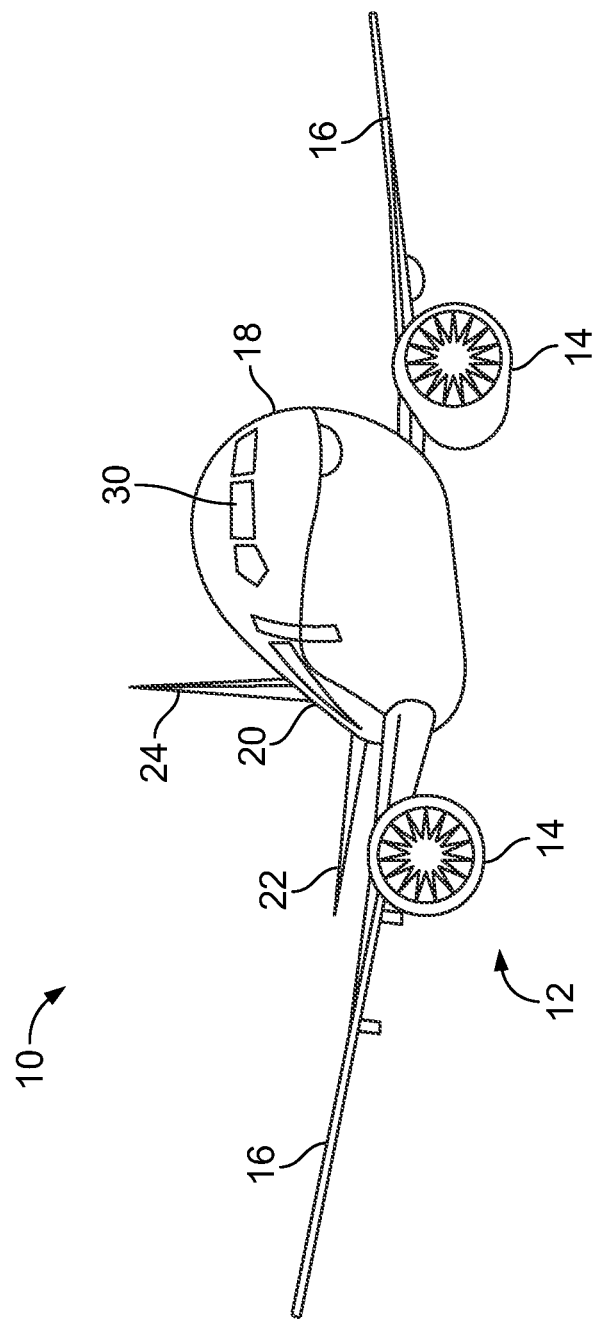
FIG. 7 illustrates a perspective front view of an aircraft, according to an example of the present disclosure.

FIG. 7 illustrates a perspective front view of an aircraft 10, according to an example of the present disclosure. The aircraft 10 includes a propulsion system 12 that includes engines 14, for example. Optionally, the propulsion system 12 may include more engines 14 than shown. The engines 14 are carried by wings 16 of the aircraft 10. In other examples, the engines 14 may be carried by a fuselage 18 and/or an empennage 20. The empennage 20 may also support horizontal stabilizers 22 and a vertical stabilizer 24.

The fuselage 18 of the aircraft 10 defines an internal cabin 30, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 30 includes one or more lavatory systems, lavatory units, or lavatories, as described herein.

The internal cabin 30 includes seat assemblies. The headrest ventilation assemblies described herein can be coupled to the seat assemblies within the internal cabin. Alternatively, instead of an aircraft, examples of the present disclosure may be used with various other vehicles, such as automobiles, buses, locomotives and train cars, watercraft, and the like. Further, examples of the present disclosure may be used with respect to fixed structures, such as commercial and residential buildings.

Figure 8A:
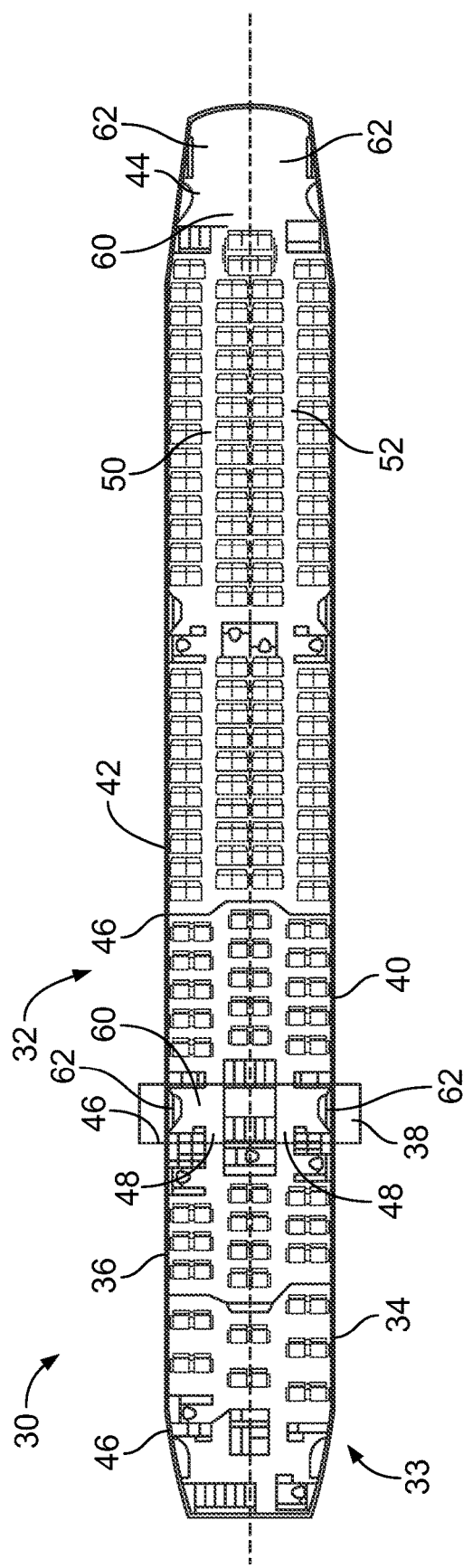
FIG. 8A illustrates a top plan view of an internal cabin of an aircraft, according to an example of the present disclosure.

FIG. 8A illustrates a top plan view of an internal cabin 30 of an aircraft, according to an example of the present disclosure. The internal cabin 30 may be within the fuselage 32 of the aircraft, such as the fuselage 18 of FIG. 7. For example, one or more fuselage walls may define the internal cabin 30. The internal cabin 30 includes multiple sections, including a front section 33, a first class section 34, a business class section 36, a front galley station 38, an expanded economy or coach section 40, a standard economy of coach section 42, and an aft section 44, which may include multiple lavatories and galley stations. It is to be understood that the internal cabin 30 may include more or less sections than shown. For example, the internal cabin 30 may not include a first class section, and may include more or less galley stations than shown. Each of the sections may be separated by a cabin transition area 46, which may include class divider assemblies between aisles 48.

As shown in FIG. 8A, the internal cabin 30 includes two aisles 50 and 52 that lead to the aft section 44. Optionally, the internal cabin 30 may have less or more aisles than shown. For example, the internal cabin 30 may include a single aisle that extends through the center of the internal cabin 30 that leads to the aft section 44.

The aisles 48, 50, and 52 extend to egress paths or door passageways 60. Exit doors 62 are located at ends of the egress paths 60. The egress paths 60 may be perpendicular to the aisles 48, 50, and 52. The internal cabin 30 may include more egress paths 60 at different locations than shown. As described herein, lavatory systems may be located at or proximate to intersections of the aisles 48, 50, 52 and the egress paths 60.

Figure 8B:
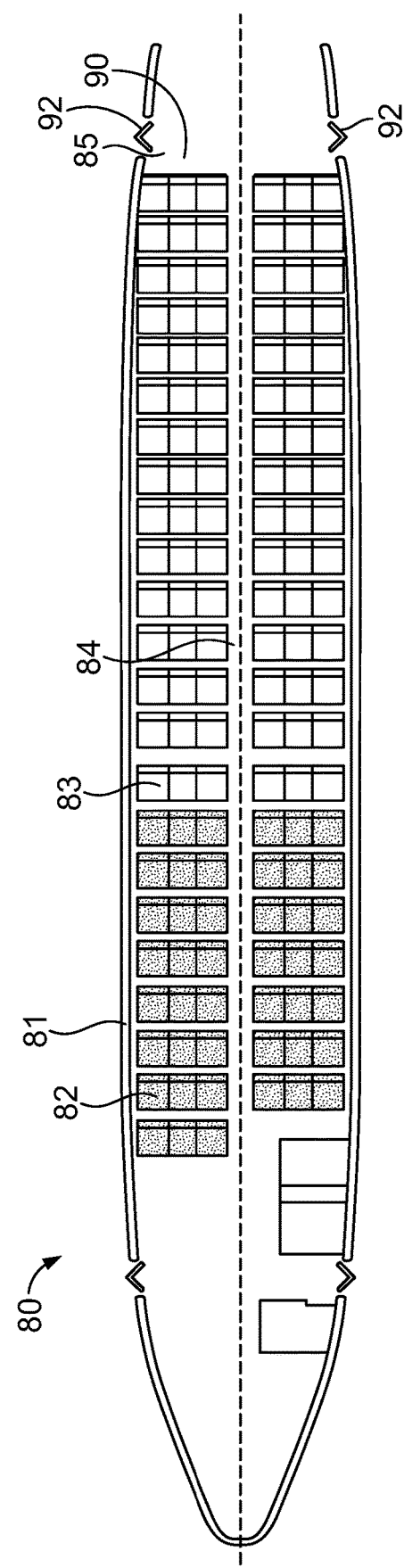
FIG. 8B illustrates a top plan view of an internal cabin of an aircraft, according to an example of the present disclosure.

FIG. 8B illustrates a top plan view of an internal cabin 80 of an aircraft, according to an example of the present disclosure. The internal cabin 80 is an example of the internal cabin 30 shown in FIG. 7. The internal cabin 80 may be within a fuselage 81 of the aircraft. For example, one or more fuselage walls may define the internal cabin 80. The internal cabin 80 includes multiple sections, including a main cabin 82 having passenger seats 83, and an aft section 85 behind the main cabin 82. It is to be understood that the internal cabin 80 may include more or less sections than shown.

The internal cabin 80 may include a single aisle 84 that leads to the aft section 85. The single aisle 84 may extend through the center of the internal cabin 80 that leads to the aft section 85. For example, the single aisle 84 may be coaxially aligned with a central longitudinal plane of the internal cabin 80.

The aisle 84 extends to an egress path or door passageway 90. Exit doors 92 are located at ends of the egress path 90. The egress path 90 may be perpendicular to the aisle 84. The internal cabin 80 may include more egress paths than shown.

Figure 9:
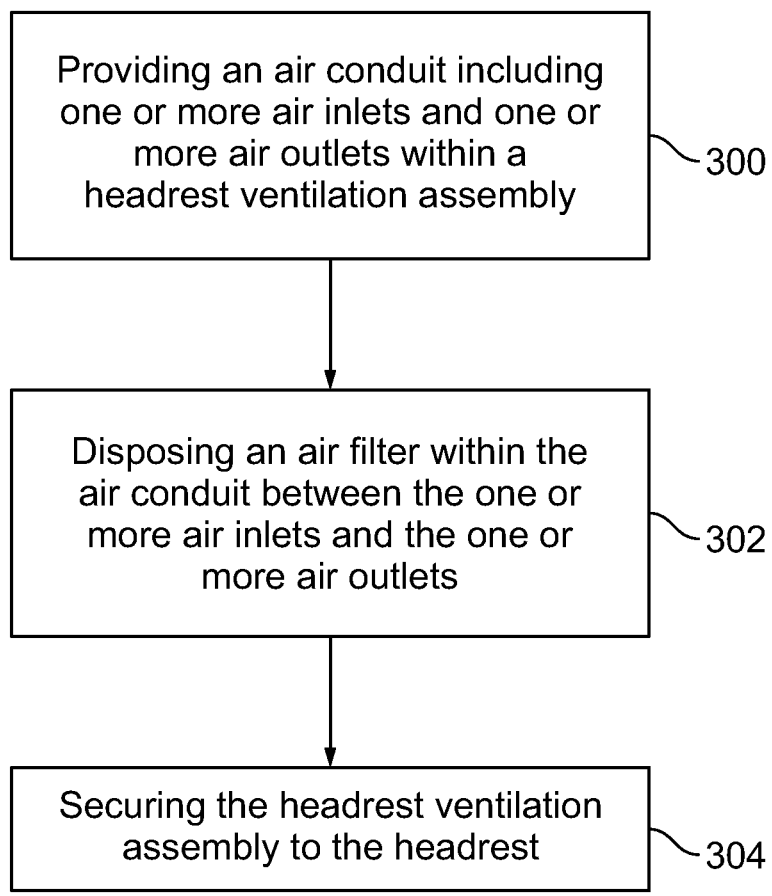
FIG. 9 illustrates a flow chart of a method for providing a headrest ventilation assembly configured to secure to a headrest of a seat assembly, according to an example of the present disclosure.

FIG. 9 illustrates a flow chart of a method for providing a headrest ventilation assembly configured to secure to a headrest of a seat assembly, according to an example of the present disclosure. The method includes providing, at 300, an air conduit including one or more air inlets and one or more air outlets within the headrest ventilation assembly; disposing, at 302, an air filter within the air conduit between the one or more air inlets and the one or more air outlets, wherein the air filter is configured to remove contaminants from the air that is drawn into the air conduit before being delivered out of the one or more air outlets; and securing, at 304, the headrest ventilation assembly to the headrest.

In at least one example, the method further includes disposing a fan on or within the air conduit. The fan is configured to draw the air into the one or more air inlets and provide airflow to deliver the air out of the one or more air outlets.

In at least one example, the method further includes disposing one or more ultraviolet (UV) light emitters on or within the air conduit. The one or more UV light emitters are configured to emit UV light into the air to sanitize the air before the air is delivered out of the one or more air outlets.

As an example, the method also includes coupling the one or more air inlets to an air source through a fluid conduit.

In at least one example, the method includes containing at least a portion of the air conduit and the air filter within a housing.

In at least one example, the method also includes fitting a covering drape of the headrest ventilation assembly over at least a portion of the headrest.

In at least one example, the method also includes providing the one or more air outlets within side wings. As a further example, the method includes moving the side wings between a stowed position and a deployed position.

As described herein, examples of the present disclosure provide systems and methods for preventing, minimizing, or otherwise reducing the spread of pathogens between passengers onboard a vehicle during a trip, such as between passengers in an internal cabin of an aircraft during a flight, without risking harm to the passengers.

Further, the disclosure comprises examples according to the following clauses:

Clause 1. A headrest ventilation assembly configured to secure to a headrest of a seat assembly, the headrest ventilation assembly comprising:
an air conduit including one or more air inlets and one or more air outlets; and
an air filter disposed within the air conduit between the one or more air inlets and the one or more air outlets, wherein the air filter is configured to remove contaminants from the air that is drawn into the air conduit before being delivered out of the one or more air outlets.

Clause 2. The headrest ventilation assembly of Clause 2, further comprising a fan disposed on or within the air conduit, wherein the fan is configured to draw the air into the one or more air inlets and provide airflow to deliver the air out of the one or more air outlets.

Clause 3. The headrest ventilation assembly of Clauses 1 or 2, further comprising one or more ultraviolet (UV) light emitters disposed on or within the air conduit, wherein the one or more UV light emitters are configured to emit UV light into the air to sanitize the air before the air is delivered out of the one or more air outlets.

Clause 4. The headrest ventilation assembly of Clause 3, wherein the UV light emitters are configured to emit the UV light at a wavelength within one or both of a far UV spectrum or a UVC spectrum.

Clause 5. The headrest ventilation assembly of any of Clauses 1-4, wherein the headrest ventilation assembly is separate and distinct from the headrest.

Clause 6. The headrest ventilation assembly of any of Clauses 1-5, wherein the one or more air inlets are coupled to an air source through a fluid conduit.

Clause 7. The headrest ventilation assembly of any of Clauses 1-6, further comprising a housing that contains at least a portion of the air conduit and the air filter.

Clause 8. The headrest ventilation assembly of any of Clauses 1-7, further comprising a covering drape that fits over at least a portion of the headrest.

Clause 9. The headrest ventilation assembly of any of Clauses 1-8, wherein the air conduit comprises one or more both of a plenum or an expandable bellows.

Clause 10. The headrest ventilation assembly of any of Clauses 1-9, further comprising side wings that include the one or more air outlets.

Clause 11. The headrest ventilation assembly of Clause 10, wherein the side wings are moveable between a stowed position and a deployed position.

Clause 12. A method for providing a headrest ventilation assembly configured to secure to a headrest of a seat assembly, the method comprising:
providing an air conduit including one or more air inlets and one or more air outlets within the headrest ventilation assembly;
disposing an air filter within the air conduit between the one or more air inlets and the one or more air outlets, wherein the air filter is configured to remove contaminants from the air that is drawn into the air conduit before being delivered out of the one or more air outlets; and
securing the headrest ventilation assembly to the headrest.

Clause 13. The method of Clause 12, further comprising disposing a fan on or within the air conduit, wherein the fan is configured to draw the air into the one or more air inlets and provide airflow to deliver the air out of the one or more air outlets.

Clause 14. The method of Clauses 12 or 13, further comprising disposing one or more ultraviolet (UV) light emitters on or within the air conduit, wherein the one or more UV light emitters are configured to emit UV light into the air to sanitize the air before the air is delivered out of the one or more air outlets.

Clause 15. The method of any of any of Clauses 12-14, further comprising coupling the one or more air inlets to an air source through a fluid conduit.

Clause 16. The method of any of Clauses 12-15, further comprising containing at least a portion of the air conduit and the air filter within a housing.

Clause 17. The method of any of Clauses 12-16, further comprising fitting a covering drape of the headrest ventilation assembly over at least a portion of the headrest.

Clause 18. The method of any of Clauses 12-17, further comprising providing the one or more air outlets within side wings.

Clause 19. The method of Clause 18, further comprising moving the side wings between a stowed position and a deployed position.

Clause 20. A system comprising:
a seat assembly including a headrest; and
a headrest ventilation assembly secured to the headrest, the headrest ventilation assembly comprising:
an air conduit including one or more air inlets and one or more air outlets; and
an air filter disposed within the air conduit between the one or more air inlets and the one or more air outlets, wherein the air filter is configured to remove contaminants from the air that is drawn into the air conduit before being delivered out of the one or more air outlets.

Clause 21. The system of Clause 20, wherein the headrest ventilation assembly further comprises a fan disposed on or within the air conduit, wherein the fan is configured to draw the air into the one or more air inlets and provide airflow to deliver the air out of the one or more air outlets.

Clause 22. The system of Clauses 20 or 21, wherein the headrest ventilation assembly further comprising one or more ultraviolet (UV) light emitters disposed on or within the air conduit, wherein the one or more UV light emitters are configured to emit UV light into the air to sanitize the air before the air is delivered out of the one or more air outlets.

While various spatial and directional terms, such as top, bottom, lower, mid, lateral, horizontal, vertical, front and the like can be used to describe examples of the subject disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described examples (and/or aspects thereof) can be used in combination with each other. In addition, many modifications can be made to adapt a particular situation or material to the teachings of the various examples of the disclosure without departing from their scope. While the dimensions and types of materials described herein are intended to define the parameters of the various examples of the disclosure, the examples are by no means limiting. Many other examples will be apparent to those of skill in the art upon reviewing the above description. The scope of the various examples of the disclosure should, therefore, be determined with reference to the appended claims, along with the full scope of equivalents to which such claims are entitled. In the appended claims and the detailed description herein, the terms "including" and "containing" are used as the plain-English equivalents of the term "comprising" and the term "in which" is used as the plain-English equivalents of the term "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various examples of the disclosure, including the best mode, and also to enable any person skilled in the art to practice the various examples of the disclosure, including making and using any devices or systems and performing any incorporated methods. The patentable scope of the various examples of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A headrest ventilation assembly configured to secure to a headrest of a seat assembly, the headrest ventilation assembly comprising:
a housing configured to removably mount onto or over the headrest, wherein the housing is selectively mountable onto or over the headrest;
an air conduit within the housing, the air conduit including one or more air inlets and one or more air outlets;
an air filter disposed within the air conduit between the one or more air inlets and the one or more air outlets, wherein the air filter is configured to remove contaminants from air that is drawn into the air conduit before being delivered out of the one or more air outlets;
a covering drape that fits over at least a portion of the headrest;
wherein the air conduit includes a plenum coupled to the covering drape, wherein the plenum fits over at least a portion of the headrest;
wherein the air conduit includes an expandable bellows coupled to the plenum, wherein the expandable bellows fits over at least a portion of the headrest, and wherein the expandable bellows is selectively lengthened or shortened to provide a desired fit; and
an adjustment member disposed on a back of the headrest, wherein the adjustment member allows the headrest ventilation assembly to be adapted to a size and shape of the headrest.

2. The headrest ventilation assembly of claim 1, further comprising a fan disposed on or within the air conduit, wherein the fan is configured to draw the air into the one or more air inlets and provide airflow to deliver the air out of the one or more air outlets.

3. The headrest ventilation assembly of claim 1, further comprising one or more ultraviolet (UV) light emitters disposed on or within the air conduit, wherein the one or more UV light emitters are configured to emit UV light into the air to sanitize the air before the air is delivered out of the one or more air outlets.

4. The headrest ventilation assembly of claim 3, wherein the UV light emitters are configured to emit the UV light at a wavelength within one or both of a far UV spectrum or a UVC spectrum.

5. The headrest ventilation assembly of claim 1, wherein the headrest ventilation assembly is separate and distinct from the headrest.

6. The headrest ventilation assembly of claim 1, wherein the one or more air inlets are coupled to an air source through a fluid conduit.

7. The headrest ventilation assembly of claim 1, further comprising side wings that include the one or more air outlets.

8. The headrest ventilation assembly of claim 7, wherein the side wings are moveable between a stowed position and a deployed position.

9. A method for providing a headrest ventilation assembly configured to secure to a headrest of a seat assembly, the method comprising:
provide an air conduit including one or more air inlets and one or more air outlets within the headrest ventilation assembly;
disposing an air filter within the air conduit between the one or more air inlets and the one or more air outlets, wherein the air filter is configured to remove contaminants from air that is drawn into the air conduit before being delivered out of the one or more air outlets;
removably securing the headrest ventilation assembly to the headrest, wherein said removably securing comprises selectively mounting the headrest ventilation assembly onto or over the headrest;
fitting a covering drape of the headrest ventilation assembly over at least a portion of the headrest;
fitting a plenum coupled to the covering drape over at least a portion of the headrest;
fitting an expandable bellows coupled to the plenum over at least a portion of the headrest, and wherein the expandable bellows is selectively lengthened or shortened to provide a desired fit; and
disposing an adjustment member on a back of the headrest, wherein the adjustment member allows the headrest ventilation assembly to be adapted to a size and shape of the headrest.

10. The method of claim 9, further comprising disposing a fan on or within the air conduit, wherein the fan is configured to draw the air into the one or more air inlets and provide airflow to deliver the air out of the one or more air outlets.

11. The method of claim 9, further comprising disposing one or more ultraviolet (UV) light emitters on or within the air conduit, wherein the one or more UV light emitters are configured to emit UV light into the air to sanitize the air before the air is delivered out of the one or more air outlets.

12. The method of claim 9, further comprising coupling the one or more air inlets to an air source through a fluid conduit.

13. The method of claim 9, further comprising containing at least a portion of the air conduit and the air filter within a housing that removably mounts onto or over the headrest.

14. The method of claim 9, further comprising providing the one or more air outlets within side wings.

15. The method of claim 14, further comprising moving the side wings between a stowed position and a deployed position.

16. The method of claim 11, wherein the UV light emitters are configured to emit the UV light at a wavelength within one or both of a far UV spectrum or a UVC spectrum.

17. A system comprising:
a seat assembly including a headrest; and
a headrest ventilation assembly secured to the headrest, the headrest ventilation assembly comprising:
a housing that removably mounts onto or over the headrest, wherein the housing is selectively mountable onto or over the headrest;
an air conduit including a plenum and an expandable bellows coupled to the plenum within the housing, the air conduit including one or more air inlets and one or more air outlets, wherein the plenum fits over at least a portion of the headrest, and wherein the expandable bellows fits over at least a portion of the headrest, and wherein the expandable bellows is selectively lengthened or shortened to provide a desired fit;
an air filter disposed within the air conduit between the one or more air inlets and the one or more air outlets, wherein the air filter is configured to remove contaminants from air that is drawn into the air conduit before being delivered out of the one or more air outlets;
a covering drape that fits over at least a portion of the headrest, wherein the plenum is coupled to the covering drape; and
an adjustment member disposed on a back of the headrest, wherein the adjustment member allows the headrest ventilation assembly to be adapted to a size and shape of the headrest.

18. The system of claim 17, wherein the headrest ventilation assembly further comprises a fan disposed on or within the air conduit, wherein the fan is configured to draw the air into the one or more air inlets and provide airflow to deliver the air out of the one or more air outlets.

19. The system of claim 17, wherein the headrest ventilation assembly further comprising one or more ultraviolet (UV) light emitters disposed on or within the air conduit, wherein the one or more UV light emitters are configured to emit UV light into the air to sanitize the air before the air is delivered out of the one or more air outlets.

20. The system of claim 19, wherein the UV light emitters are configured to emit the UV light at a wavelength within one or both of a far UV spectrum or a UVC spectrum.

* * * * *